US010117470B2

(12) United States Patent
Reese et al.

(10) Patent No.: US 10,117,470 B2
(45) Date of Patent: Nov. 6, 2018

(54) MEDICAL GOWN WITH ADJUSTABLE TIE STRAPS

(71) Applicant: Prestige Ameritech, Ltd., North Richland Hills, TX (US)

(72) Inventors: George Daniel Reese, North Richland Hills, TX (US); Donna L. Reese, North Richland Hills, TX (US)

(73) Assignee: Prestige Ameritech, Ltd., North Richland Hills, TX (US)

( * ) Notice: Subject to any disclaimer, the term of this patent is extended or adjusted under 35 U.S.C. 154(b) by 105 days.

(21) Appl. No.: 14/726,482

(22) Filed: May 30, 2015

(65) Prior Publication Data

US 2016/0345645 A1    Dec. 1, 2016

(51) Int. Cl.
*A41D 13/12* (2006.01)
*A61B 90/00* (2016.01)

(52) U.S. Cl.
CPC .......... *A41D 13/1209* (2013.01); *A61B 90/00* (2016.02); *A41D 13/129* (2013.01)

(58) Field of Classification Search
CPC .............. A41D 13/1209; A41D 13/129; A41D 2400/52; A41D 2400/44; A41D 13/12; A61B 19/00
USPC ..... 2/114, 128, 105, 311, 312, 318, 338, 48, 2/49.1, 49.2, 49.3, 49.4, 49.5, 52; D2/720, 861
See application file for complete search history.

(56) References Cited

U.S. PATENT DOCUMENTS

| | | | | |
|---|---|---|---|---|
| 3,146,465 A | * | 9/1964 | Hummel | A41B 13/10 2/49.3 |
| 3,230,546 A | * | 1/1966 | Sabee | A41D 13/1209 2/114 |
| 3,594,818 A | * | 7/1971 | Planner | A41D 13/1209 2/114 |
| 3,648,290 A | * | 3/1972 | Hartigan | A41D 13/1209 2/114 |
| 3,696,443 A | * | 10/1972 | Taylor | A41D 13/1209 2/114 |
| 3,754,284 A | * | 8/1973 | Hartigan | A41D 13/1209 2/114 |
| 3,988,781 A | * | 11/1976 | Horan | A41D 13/1209 2/114 |
| 4,016,604 A | * | 4/1977 | Welke | A41D 13/1209 2/51 |

(Continued)

*Primary Examiner* — Alissa Tompkins
*Assistant Examiner* — Griffin Hall
(74) *Attorney, Agent, or Firm* — Betsy Kingsbury Dowd, Esq.; BKDowd Law, P.C.

(57) ABSTRACT

A medical gown includes tie straps detachably connected to sleeves of the gown. The straps are detachable by tugging on them once the gown is donned. The tie members are extendable, upon being detached, around the left and right sides to a back of the medical gown for tying together to form a closure around a waist of a wearer. The tie members may be sufficiently long to extend back around for tying in the front of the gown. A section of each of the left and right tie straps may be folded over lengthwise, a portion of the folded section of each tie member being detachably connected to the sleeves. Once the wearer detaches the folded tie members, the tie members may be unfolded and elongated as needed for adjustably sizing the closure securing the medical gown on the wearer.

17 Claims, 6 Drawing Sheets

(56) References Cited

U.S. PATENT DOCUMENTS

| | | | | |
|---|---|---|---|---|
| 4,017,909 A | * | 4/1977 | Brandriff | A41D 13/1209 2/158 |
| 4,075,716 A | * | 2/1978 | Collins | A41D 13/1209 2/114 |
| 4,171,542 A | * | 10/1979 | Cox | A41D 13/1209 2/114 |
| 4,326,300 A | * | 4/1982 | Bolton | A41D 13/1209 2/114 |
| 4,395,782 A | * | 8/1983 | Reynolds | A41D 13/1209 2/114 |
| 4,829,602 A | * | 5/1989 | Harreld | A41D 13/1209 2/113 |
| 4,951,318 A | * | 8/1990 | Harreld | A41D 13/1209 2/48 |
| 5,025,501 A | * | 6/1991 | Dillon | A41D 13/1209 2/51 |
| 5,444,873 A | * | 8/1995 | Levin | A41D 13/1236 2/114 |
| 5,740,552 A | * | 4/1998 | Smith | A41D 13/04 2/48 |
| 6,378,136 B2 | * | 4/2002 | Matsushita | A41D 13/1209 2/114 |
| D533,982 S | | 12/2006 | Graneto, III | |
| D598,638 S | | 8/2009 | Graneto, III | |
| 7,971,274 B2 | | 7/2011 | Graneto, III | |
| 8,701,215 B2 | * | 4/2014 | Levine | A41D 13/12 2/114 |
| 2007/0028343 A1 | | 2/2007 | Makowka | |
| 2013/0036526 A1 | * | 2/2013 | Rashman | A41D 13/1245 2/114 |
| 2013/0105511 A1 | * | 5/2013 | Graneto, III | A47F 1/08 221/303 |
| 2013/0191960 A1 | * | 8/2013 | Pasko | A41D 13/12 2/114 |
| 2013/0318682 A1 | * | 12/2013 | Graneto, III | A41D 13/1236 2/114 |
| 2016/0345644 A1 | * | 12/2016 | Reese | A41D 13/1209 |
| 2016/0345645 A1 | * | 12/2016 | Reese | A41D 13/1209 |

\* cited by examiner

MEDICAL GOWN WITH ADJUSTABLE TIE STRAPS

CROSS-REFERENCE TO RELATED APPLICATION

The present disclosure is related to a co-owned U.S. nonprovisional patent application filed on even day herewith, entitled ADJUSTABLY SIZED MEDICAL GOWN having named inventors George Daniel Reese and Donna L. Reese, Ser. No. 14/726,487, referred to herein as "Related Application," the entirety of which is incorporated herein by reference.

TECHNICAL FIELD

The present disclosure relates generally to medical gowns and, in particular, to a medical gown having adjustable tie straps.

BACKGROUND

Medical gowns for use by various health care workers, as well as by hospital visitors, are well-known in the art. Such protective wear may be designed to provide various levels of protection depending on the particular use and potential contaminants that the health care worker may be exposed to. At the least, a medical gown should shield the wearer's clothes and skin from direct contact with any bodily fluids or medical waste that may be contaminated with germs or viruses. To insure that the wearer does not transfer any germs or viruses to the wearer's clothes or person, a medical gown is commonly affixed in place on the wearer using ties. Preferably, the medical gown is appropriately fitted on the wearer for use, such that no portions of the gown may loosely drape or inadvertently contact contaminated surfaces or substances. The ties themselves, however, can be a source of potential contamination if they inadvertently dangle onto a floor or other surface harboring germs or viruses. This is a difficult problem to avoid, particularly since the ties that are provided on the gown also need to be long enough to secure around healthcare workers of larger stature and short enough not to dangle on the ground when secured around persons of smaller stature.

A need exists, therefore, for medical gowns that minimize the risk of exposure to healthcare workers of contaminants. A need also exists for medical gowns that decrease the risk of exposure to healthcare workers of contaminants while also being adjustable in size to accommodate health care workers of varying stature.

SUMMARY

Features of the disclosure will become apparent from the following detailed description considered in conjunction with the accompanying drawings. It is to be understood, however, that the drawings are designed as an illustration only and not as a definition of the limits of this disclosure.

The present disclosure is directed to a medical gown that decreases the risk of exposure to healthcare workers of contaminants. The present disclosure is also directed to a medical gown that minimizes the risk of exposure to healthcare workers of contaminants while also being adjustable in size to accommodate health care workers of various stature.

In aspects, the present disclosure is directed to a medical gown that includes a torso portion comprising a front portion and a left and a right side portion connected to opposing sides of the front portion. An upper portion extends upward from the torso portion. The upper portion includes a left arm member and a right arm member configured to cover a left and right arm, respectively, of a wearer of the medical gown. The upper portion further includes an opening configured to fit around a wearer's neck.

The upper portion further includes a tie member extending on one end from one of the left and right side portions, with a section of the tie member folded over lengthwise. A portion of the folded section is detachably connected to one of the left and right arm members that is proximate the one end. Once detached by a wearer from the one of the left and right arm members, the tie member is operable to unfold and elongate for tying around a waist of the wearer.

In one aspect, the tie member includes a first section and a second section, which are joined to form a folded edge. The tie member is lengthwise folded and unfolded along the folded edge.

The folded edge may be formed from bonding ends of the first section and the second section together.

In another aspect, the tie member is a first tie member extending from the left side portion proximate the left arm member. The first tie member is detachably connected to the left arm member. The medical gown further includes a second tie member extending from the right side portion proximate the right arm member. A section of the second tie member is folded over lengthwise. A portion of the folded section of the second tie member is detachably connected to the right arm member. Upon being detached from the right arm member by the wearer, the second tie member is operable to unfold and elongate for tying around the wearer.

Each of the first tie member and the second tie member may be operable to extend around the left and the right side portions and to tie together to form a closure around the wearer. A size of the closure is adjustable by unfolding one or both of the first tie member and the second tie member being tied together.

In still another aspect, the detachably connected portion is formed from a perforated section of material connecting the one of the left and the right arm members to the tie member.

In yet another aspect, the detachably connected portion is formed from one of a weak seam, an adhesive, and loose stitches connecting the one of the left and the right arm members to the tie member.

In a further aspect, the upper portion includes a back side and a front side, wherein the right and the left arm members are formed by joining a portion of a bottom edge of each of the back side and the front side to form an enclosure for covering a wearer's arms.

The tie member may include a first section and a second section, which are joined to form a folded edge. The tie member is lengthwise folded and unfolded along the folded edge.

A top edge of the first section may be detachably connected along the bottom edge of the front side and a top edge of the second section may be detachably connected along the bottom edge of the back side.

In another aspect of the medical gown, no portion of the detachably connected tie member on the medical gown donned by a wearer, before being detached from the one of the left and right arm members, hangs below a bottom edge of the torso portion.

The medical gown, in aspects, may be formed of a material comprising polyethylene coated spunbond polypropylene.

In some aspects, the medical gown is formed of a material and of a construction to provide fluid resistant protection to a wearer of the medical gown.

The material may further include an antimicrobial agent.

Each of the right and left arm members in aspects of the gown is a full-length sleeve for fitting a wearer's arm therethrough and having an opening for at least a portion of a wearer's hand.

In some aspects, the sleeves further include a second opening for fitting a wearer's thumb therethrough.

In additional aspects, each of the first and second tie members upon being detached and unfolded, is sufficiently long to extend around the left and right sides, respectively, to the back of the medical gown, and further around the right and left sides, respectively, to tie together along the front side of the medical gown.

The present disclosure is also directed to a medical gown that includes a torso portion and an upper portion extending upward from the torso portion. The torso portion includes a front portion and a left and a right side portion connected to opposing sides of the front portion. The upper portion includes a left arm member and a right arm member configured to cover a left and right arm, respectively, of a wearer of the medical gown. The upper portion further includes an opening configured to fit around a wearer's neck. The medical gown also includes a left tie member extending on one end from the left side portion proximate the left arm member, and a right tie member extending on one end from the right side portion proximate the right arm member. A second end of the left tie member is detachably connected to the left arm member, and a second end of the right tie member is detachably connected to the right arm member. The left and right tie members are extendable, upon being detached, around the left and right sides to a back of the medical gown for tying together to form a closure around a waist of a wearer.

In an additional aspect, each of the left and right tie members upon being detached is sufficiently long to not only extend around the left and right sides, respectively, to the back of the medical gown, but to also further extend around the right and left sides, respectively, to tie together along the front side of the medical gown.

In one aspect, a section of each of the left and right tie members is folded over lengthwise. A portion of the folded section of the left tie member is detachably connected to the left arm member and a portion of the folded section of the right tie member is detachably connected to the right arm member. Each of the right and left tie member is operable upon being detached to unfold and elongate for adjustably sizing the closure securing the medical gown on the wearer.

In another aspect, each tie member includes a first section and a second section, which are joined to form a folded edge. Each tie member is lengthwise folded and unfolded along the folded edge.

In still another aspect, the folded edge is formed from bonding ends of the first section and the second section together.

In addition to the above aspects of the present disclosure, additional aspects, objects, features and advantages will be apparent from the embodiments presented in the following description and in connection with the accompanying drawings.

BRIEF DESCRIPTION OF THE DRAWINGS

The drawings constitute a part of this disclosure and include examples, which may be implemented in various forms. It is to be understood that in some instances, various aspects of the disclosure may be shown exaggerated or enlarged to facilitate understanding. The teaching of the disclosure can be readily understood by considering the detailed description in conjunction with the accompanying drawings, which are briefly described below.

The various aspects of the present disclosure mentioned above are described in further detail with reference to the aforementioned figures and the following detailed description of exemplary embodiments.

DETAILED DESCRIPTION

Particular illustrative embodiments of the present disclosure are described hereinbelow with reference to the accompanying drawings; however, the disclosed embodiments are merely examples of the disclosure, which may be embodied in various forms. It should be apparent to those skilled in the art that the described embodiments provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present disclosure of a medical gown as defined herein and equivalents thereto. Well-known functions or constructions and repetitive matter are not described in detail to avoid obscuring the present disclosure in unnecessary or redundant detail. Therefore, specific structural and functional details disclosed herein are not to be interpreted as limiting. In this description, as well as in the drawings, like-referenced numbers represent elements which may perform the same, similar, or equivalent functions.

Throughout the description, where items are described as having, including, or comprising one or more specific components or features, or where methods are described as having, including, or comprising one or more specific steps, it is contemplated that, additionally, there are items of the present disclosure that consist essentially of, or consist of, the one or more recited components or features, and that there are methods according to the present disclosure that consist essentially of, or consist of, the one or more recited processing steps.

The present disclosure is directed to a medical gown that may reduce the risk of exposure to healthcare workers of contaminants. The present disclosure is also directed to a medical gown that may reduce the risk of exposure to healthcare workers of contaminants while also being adjustable in size to accommodate health care workers of various stature. The embodiments described herein are directed to improvements to a type of a medical gown which may be referred to as a "personal protection gown." Although the medical gown of the embodiments shown does not fully cover a wearer's back, as one of ordinary skill in the art will recognize, the present disclosure is not, however, limited thereto. Accordingly, the gown of the present disclosure may be constructed with a full back layer and other features, for example, to comply with different levels of AAMI ("Association for the Advancement of Medical Instrumentation") protection. In embodiments, the medical gown of the present disclosure may include gowns of varying lengths, as well as gowns that fully cover the back as well as the front of a wearer, and, optionally, the head. In addition, while the embodiments described are directed to a gown that is donned over the wearer's head, the scope of the claims is not limited to the particular configuration shown. For example, the medical gown of the present disclosure may include, but is not limited to, personal protection gowns, surgical gowns, isolation gowns, and so on, including gowns formed of the appropriate materials and of the appropriate construction as to provide the desired level of fluid resistant and/or fluid impervious protection to the wearer. The medical gown of the present disclosure may also be formed of a material that comprises antitoxins and/or antimicrobials.

"Ties," "tie straps," and "tie members" are used interchangeably herein to refer to a long narrow strip of material used for binding or securing the medical gown on a wearer by tying.

Figure 1:
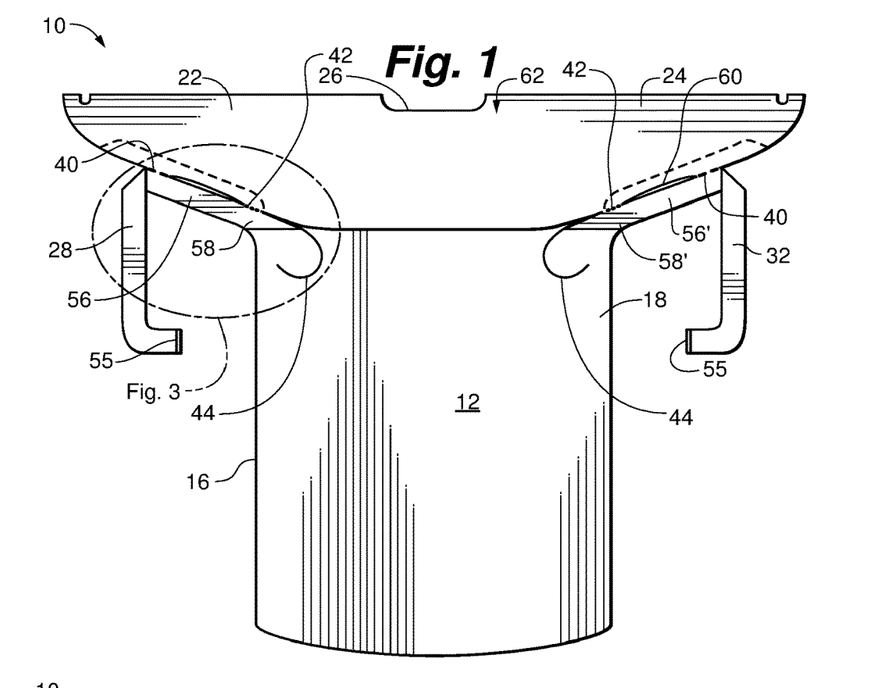
FIG. 1 is a pictorial representation of a back view of an embodiment of a medical gown of the present disclosure.
Figure 2:
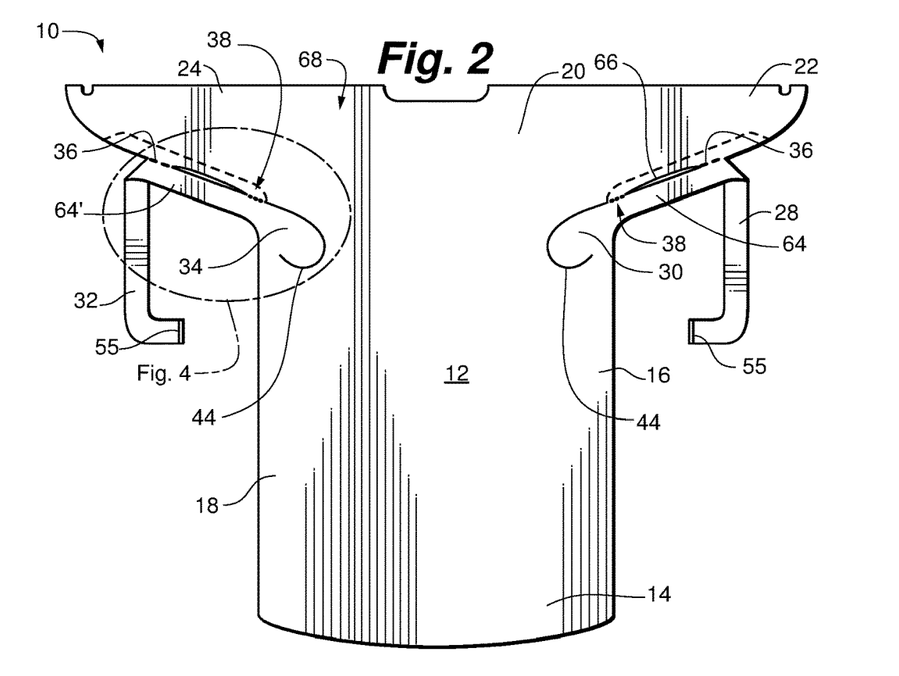
FIG. 2 is a pictorial representation of a front view of the embodiment of the medical gown of FIG. 1.

Referring to FIGS. 1 and 2, embodiments of a medical gown 10 of the present disclosure include a torso portion 12. The torso portion 12 includes a front portion 14 and a left 16 and a right side portion 18 connected to opposing sides of the front portion 14. The medical gown 10 also includes an upper portion 20, which extends upward from the torso portion 12 to cover the shoulders and arms of a wearer of the gown. In embodiments, the upper portion 20 includes a left arm member 22 and a right arm member 24 configured to cover a left and right arm, respectively, of a wearer of the medical gown. In particular embodiments, the left and right arm members are full length sleeves that extend over the arms and may also extend over substantial portions of the hands of a wearer. The upper portion 20 of the medical gown 10 further includes an opening 26 appropriately sized for fitting around a wearer's neck and in the embodiment shown, for fitting a wearer's head therethrough for donning the gown over one's head.

Referring still to FIGS. 1 and 2, the medical gown 10 further includes a tie member 28 that extends on one (first) end 30 from, and which may be integral with, the left side portion 16. The medical gown 10 may further include another tie member 32 that extends on one fits first) end 34 from, and which may be integral with, the right side portion 18.

Figure 3:
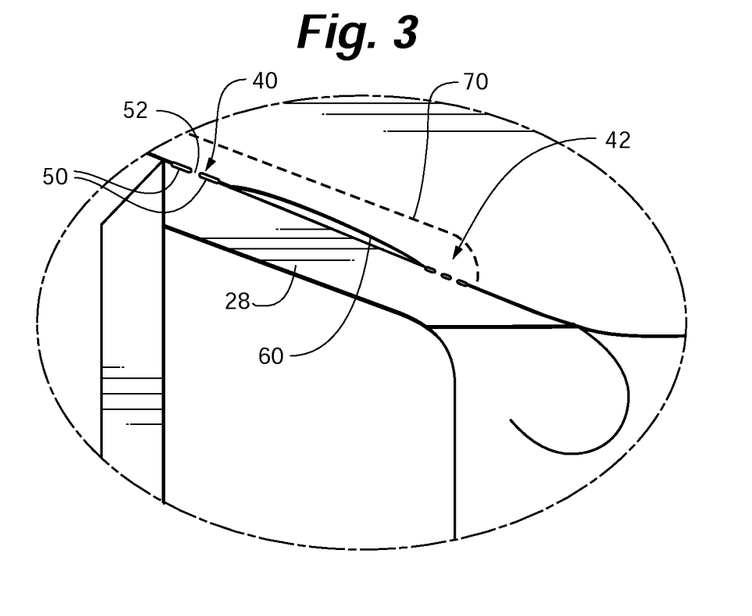
FIG. 3 is an enlarged view of an embodiment of the encircled area of FIG. 1.
Figure 4:
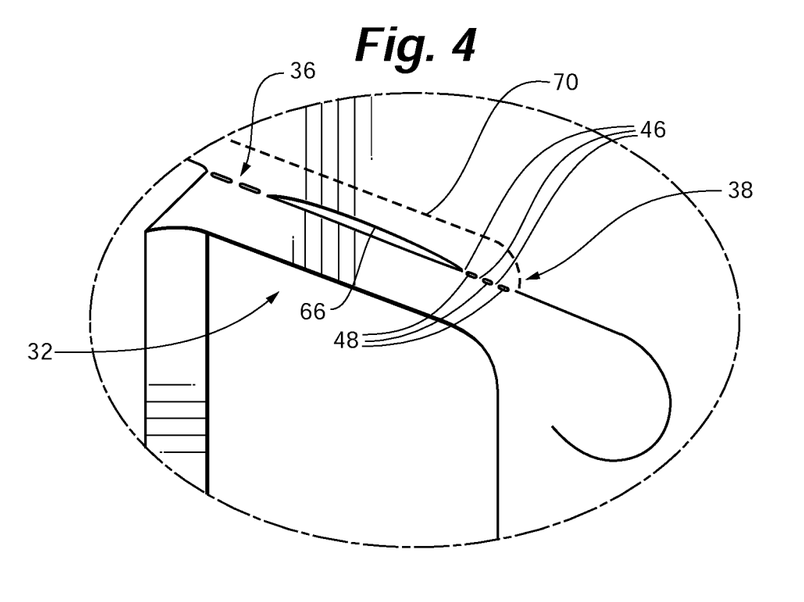
FIG. 4 is an enlarged view of an embodiment of the encircled area of FIG. 2.

In embodiments, each tie member is detachably connected to its respective proximate arm member. Referring to FIGS. 3 and 4 as well as to FIGS. 1 and 2, embodiments of the medical gown of the present disclosure are configured to allow a wearer to don the gown without the tie straps dangling on the floor, thereby helping to reduce the worker's risk of contacting contaminants. In addition, by connecting tie members 28 and 32 to the arm members 22 and 24, respectively, the wearer does not have to struggle to reach and find them each time a gown is used, as is the case with other gowns which have straps that loosely dangle. On the contrary, each tie member 28 and 32 is reliably fixed on at least one portion of the respective arm member 22, 24 that is easy to access for detachment by the wearer. This allows any wearer to quickly and easily don the gown, access the straps, and secure them around the wearer's waist by tying.

Figure 5:
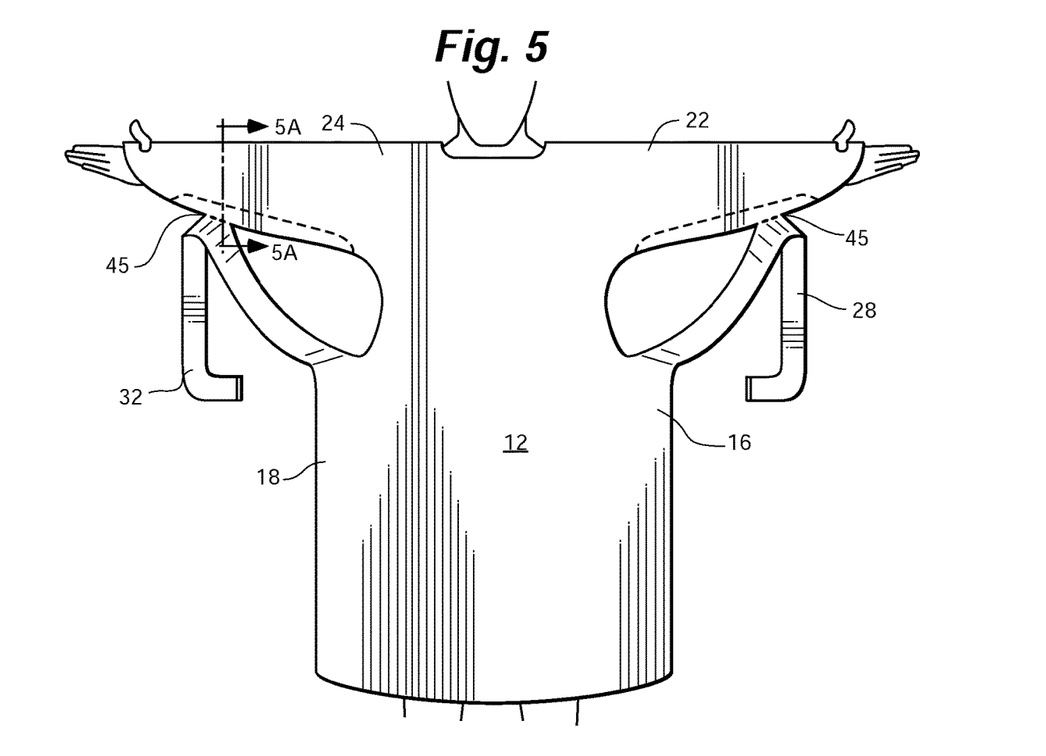
FIG. 5 is a pictorial representation of a front view of the embodiment of the medical gown of FIG. 1, as donned by a wearer, with each strap still detachably secured to a sleeve of the gown.

Referring still to FIGS. 1-4, tie members 28 and 32 may be detachably connected at one or more portions to the arm members 22, 24. Referring also to FIG. 5, at least one portion 45 that is easily accessible by the wearer preferably stays attached after the wearer dons the gown. The wearer may then reach across with one (left/right) hand to the opposite (right/left) arm to tug on and remove the connected portion 45 from each arm member 22, 24. Once the wearer disconnects the tie straps 28, 32 from the respective arm members 22, 24, the wearer may extend each tie member 28, 32 around each of the left 16 and the right side portions 18, respectively, and tie them together to form a closure around the wearer for securing the gown.

In embodiments, the detachably connected portions 45 are formed from a perforated section of material connecting the tie member to the respective (proximate) arm member. In particular embodiments described below, detachably connected portions 45 include front 36 and back portions 40, which, as shown in FIGS. 1-4, may each include perforated sections.

In other embodiments, the detachably connected portions 45 may be formed from a weak seam, an adhesive, or loose stitches connecting the tie member to the respective (proximate) arm member.

Referring to FIGS. 1-4, additional detachably connected portions 38, 42 located closer to the front portion 14 than portions 45, may weakly connect the tie members 28, 32 to arm members 22, 24. In embodiments, the additional portions 38, 42 are configured to break away easily as the wearer dons the gown 10, leaving only connected portions 45 intact, as shown in FIG. 5.

In the embodiments shown in FIGS. 1-4, additional portions 38, 42 may represent a front and back detachably connected section, respectively, each of which may have a differently configured perforated pattern or otherwise be configured to break-away with more or less ease. The additional portions 38, 42, in different embodiments, may represent a single perforated or otherwise weakly connected section in a single layer of material extending from each sleeve 22, 24.

As shown in FIG. 3 and FIG. 4, connected portions 38, 42 may include one or more small continuous points, or tacks 46, between the tie member and proximate arm member, separated by perforations 48, or discontinuous edges or breaks between the tie member and proximate arm members, that are sufficiently large to allow the tacks 46 to easily break upon the wearer donning the gown. As shown in FIGS. 3 and 4, in embodiments of the medical gown 10 of the present disclosure, portions 45, which include portions 36, 40 in this embodiment, may provide a stronger connectivity, requiring the wearer to tug on each tie member to disconnect it from the proximate arm member after donning the gown. For example, the perforated sections 50 may be smaller than adjacent connecting sections 52.

The medical gown 10 of the present disclosure may also include cut-outs to aid in fitting the gown around the wearer. For example, curved cut-outs 44 may be provided in the torso portion 12 proximate the ends 30, 34 of the tie members. When the wearer extends the tie members back around the side portions 16, 18, the side portions separate from the arm members along cut-outs 44, so that the side portions 16, 18 can wrap around the sides and back of a wearer.

Although not shown, the side portions may be weakly tacked to the front portion 14 along the cut-outs 44. For example, a few, small, scattered points of continuity between the front portion 14 and proximate side portion 16, 18 may be provided along the cut-out 44. The side portions 16, 18 easily break away along the cut-outs 44 upon donning the gown 10 and/or when the wearer extends the tie members back around the side portions 16, 18 for tying.

Figure 5A:
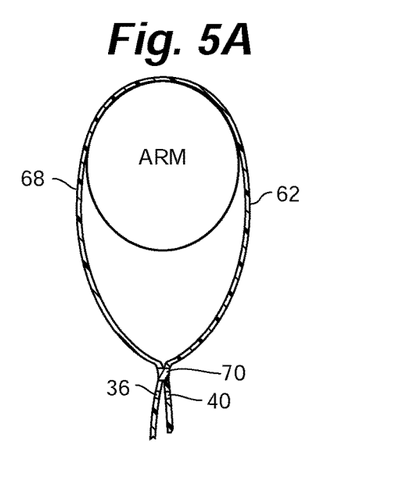
FIG. 5A is a cross-sectional view of an arm member of FIG. 5.

Referring still to FIGS. 1-5A, the upper portion 20 of the medical gown 10 may include a back side 62 and a front side 68. In embodiments, the arm members 22, 24 are formed by joining a portion of a bottom edge 60, 66 of each of the back side 62 and the front side 68 to form an enclosure to cover a wearer's arms. The seam for joining the arm members may be formed by any appropriate means in the art, including heat sealing, stitching, adhesives, and so on. As shown in FIGS. 3, 4, and 5A, in embodiments, the seams 70 may be formed on the outer surfaces of the gown, such that the bottom edge 60, 66 of each of the back side 62 and the front side 68 remain exposed and are attached to the tie members 28, 32.

Figure 6A:
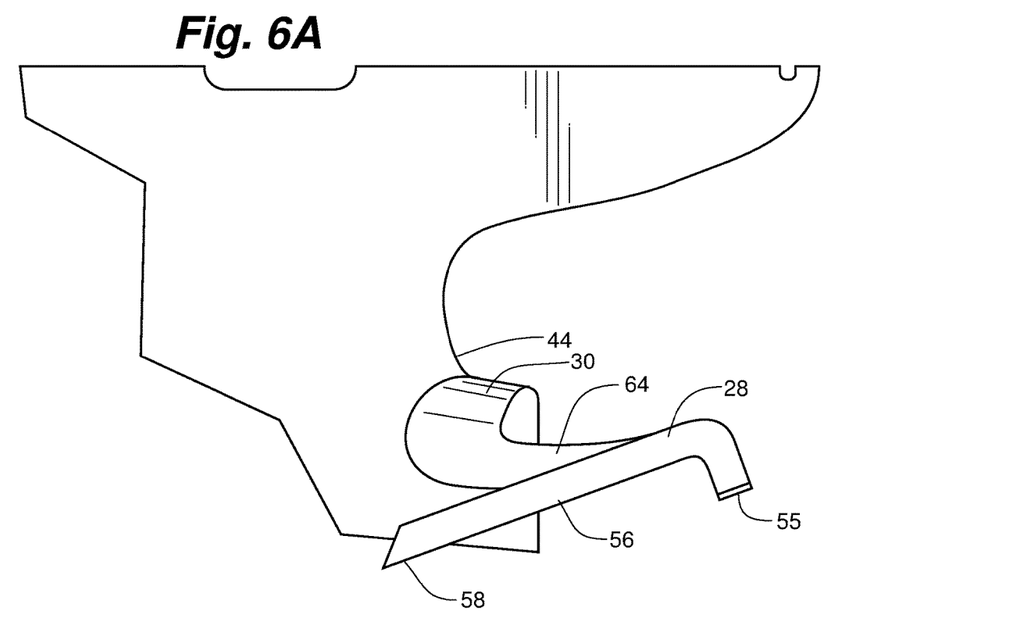
FIG. 6A is a pictorial representation of a front view of the embodiment of the medical gown of FIG. 1, with the left strap detached from the sleeve of the gown.
Figure 6B:
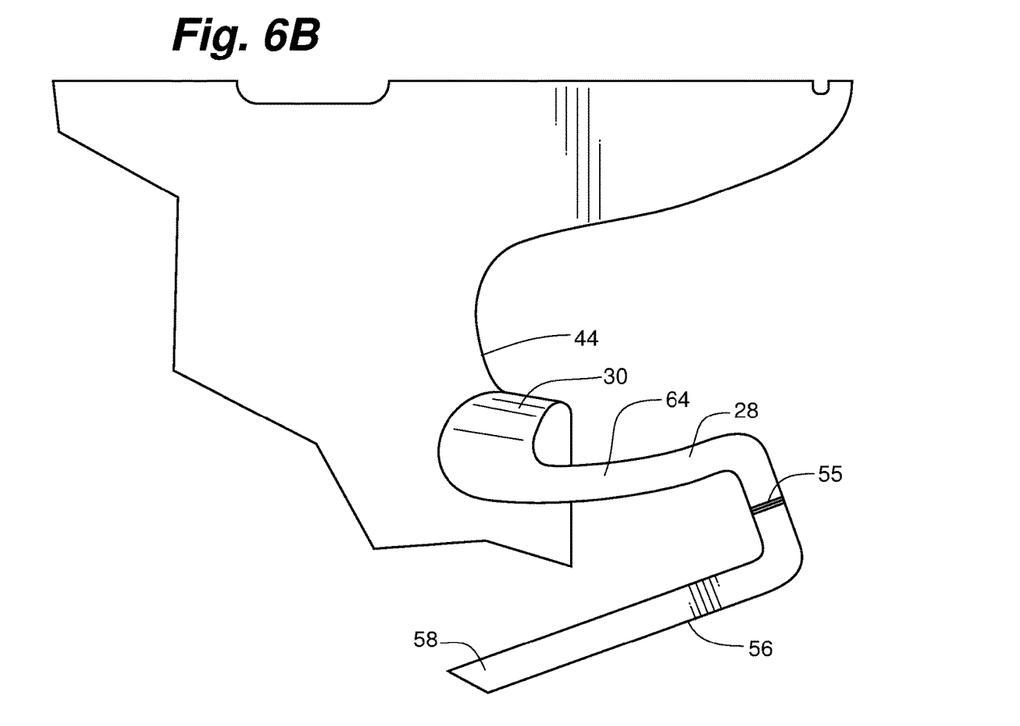
FIG. 6B is a pictorial representation of an embodiment of the medical gown of FIG. 6A, with the left strap detached and unfolded for elongation.
Figure 7A:
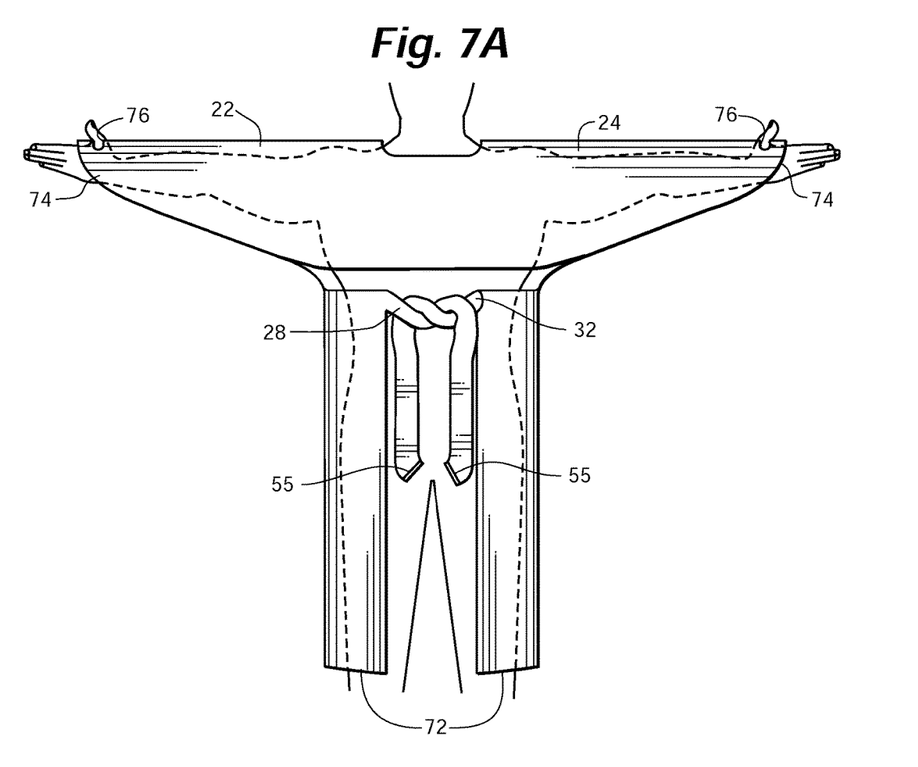
FIG. 7A is a pictorial representation of a back view of an embodiment of the medical gown of FIG. 1 closed and tied around a wearer in a first configuration.
Figure 7B:
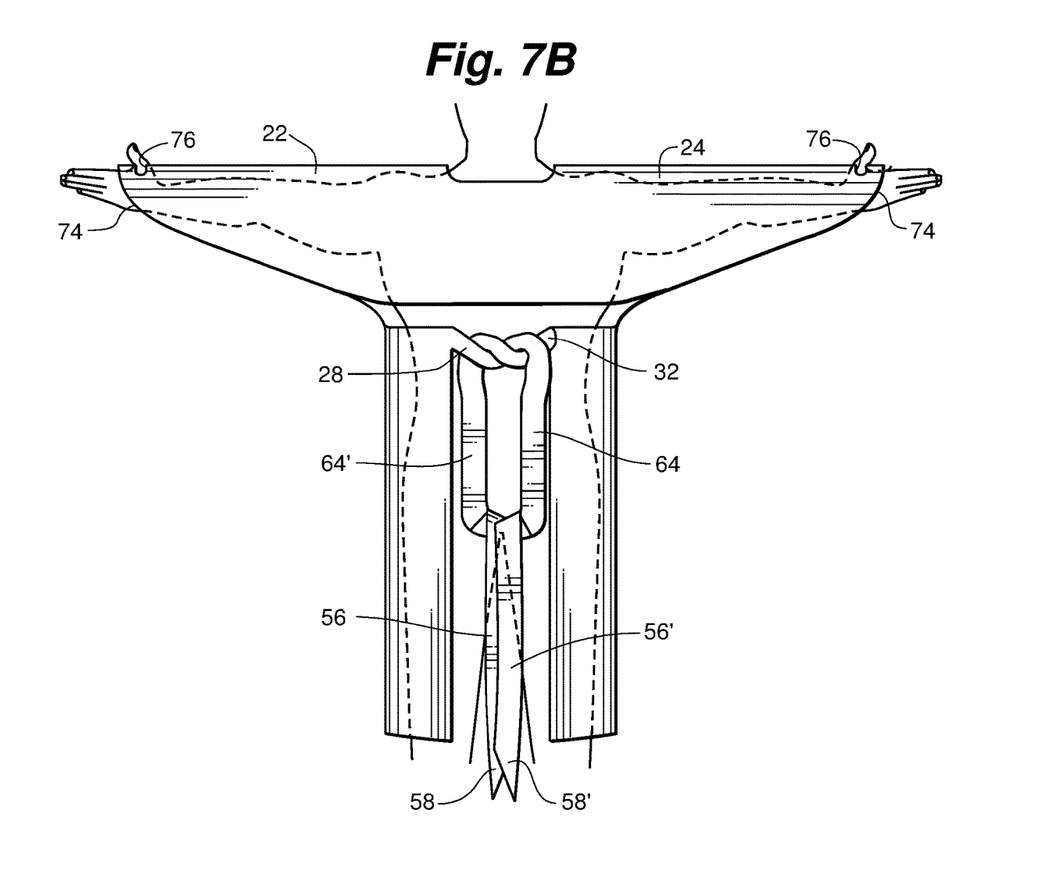
FIG. 7B is a pictorial representation of a back view of an embodiment of the medical gown of FIG. 1 closed and tied around a wearer in a second configuration.

Referring also to FIGS. 6A and 6B, in embodiments, each tie member 28, 32 includes a folded edge 55 about which a lengthwise (first) section 56 of the tie member is folded. In embodiments, first section 56 and at least one (second) section 64 onto which first section 56 is folded are detachably connected to arm members 22, 24, at least at one portion 45 as described above. Once the tie members 28, 32 are detached by the wearer, one or more folded sections may be unfolded and elongated for tying around a waist of the wearer. Optionally, as shown in FIG. 7A, for example, if the wearer is of small stature, the tie members may be detached from the arm members, and remain folded around folded edge 55 while extended around the wearer and tied together to form a smaller closure. FIG. 7B shows the tie members unfolded and partially tied, in one configuration, in a double knot, before being tightened around the user. As should be apparent from FIG. 7B, when the tie members are extended in their unfolded state, the size of the closure is adjustable to fit a person of larger stature than when used in the folded state of FIG. 7A. By unfolding one or more sections of one or both of the left tie member 28 and the right tie member 32 for tying together around the waist of the wearer, the size of the closure is adjustable. In addition, preferably in both configurations of FIGS. 7A and 7B, when the length of the tie members is appropriately adjusted to the wearer's stature, the tie members will not dangle onto the floor.

In embodiments, the tie members are preferably sufficiently long, once unfolded, to extend around each of the left and right sides, respectively, to the back of the medical gown, and to further extend back around each of the right and left sides, respectively, back to the front of the gown. In this configuration, most wearers can optionally advantageously tie the straps together in the front of the medical gown. This affords great flexibility to the user in adjusting the fit of the gown, and in adjusting the amount of excess strap length after tying.

In embodiments, a medical gown may also include a single (folded in two as shown in the figures) or multiple folded tie member detachably connected proximate either a left or right arm member in accordance with the present disclosure. Once unfolded, the tie member is long enough to extend entirely around the gown for tying its loose (second) end 58, 58' back onto itself, for example, back onto the end 30, 34, respectively, that extends from the side portion 16, 18. Optionally, a loop (not shown) may be provided on the front portion 12, around which the loose (second) end 58, 58' may be tied.

In some embodiments, each of the folded sections 56 and 64 is separately attached to the bottom edge 60, 66, of the back 62 and front sides 68, respectively, of the tie members, as also shown in FIG. 5A. For example, referring to FIGS. 1 and 3, as well as to FIG. 5A, a (second) end 58, 58' of the tie member 28, 32 may be detachably connected at a portion 42 along the bottom edge 60 of a back side 62 of each arm member 22, 24. In embodiments, at least a portion 40 of the folded length 56 is detachably connected, for example, along the bottom edge 60 and preferably remains connected, upon a wearer donning the gown 10, requiring the wearer to tug on the tie member for detaching and extending around one's waist to form a closure, as described above.

Referring to FIGS. 2 and 4, at least a portion 36 of section 64 of each of the tie members is detachably connected, for example, along a bottom edge 66 of a front side 68 of each arm member 22, 24 and preferably remains connected, upon a wearer donning the gown 10, requiring the wearer to tug on the tie member for detaching and extending around one's waist to form a closure, as described above. In embodiments, the section 64 of each tie member may be detachably connected at additional portions 38 along the bottom edge 66.

In some embodiments, the sections 56 and 64 of each tie member are bonded together at one end to form the folded edge 55. Accordingly, sections 56 and 64 may be formed from separate strips of material.

In embodiments, sections 56 and 64 are bonded together with an adhesive.

In embodiments of a medical gown of the present disclosure, referring to FIG. 7A, for example, no portion of either of the detachably connected tie members 28, 32 on the medical gown donned by a user, before being detached from the respective arm members 22, 24, hangs below a bottom edge 72 of the torso portion 12.

In further embodiments, each of the right 22 and left arm members 24 is a full-length sleeve for fitting a wearer's arm therethrough, and includes an opening 74 for at least a portion of a wearer's hand. Preferably, a second opening 76 is also provided for fitting a wearer's thumb therethrough.

In other embodiments, an elasticized cuff around the wrist area, or any other appropriate means may be employed instead of the thumb opening shown to keep the arm members and gown in place on a user.

The medical gown may be formed of any suitable material. In embodiments, the medical gown is formed of a synthetic material.

In embodiments, the material comprises polyethylene coated spunbond polypropylene.

The material, along with the construction of the gown, may provide a fluid resistant gown. Higher levels of protection may be provided as described above by appropriate choice of materials and construction.

In other embodiments, at least portions of the medical gown is formed of a natural or nonsynthetic material.

In some embodiments, the material may further include an antimicrobial or antitoxin agent.

The medical gown of the present disclosure can be manufactured using any suitable method known in the art. For example, starting with a single layer of material cut into an appropriate shape for forming the front and back of the gown and arm members, a section of the material is folded along the neck line to create the two layers that will comprise the front and back of the gown. This two layer section will then be bonded as needed (along line 70 as shown in the figures, for example) to create the arm sleeves and the attachment strap(s). Bonding of the materials can be achieved by the use of adhesives, heat and pressure, ultrasonics, or any other suitable means. In this way, portions of the folded section below the seam 70 form the extendable strap(s), which are then die cut by commercially available means such as flatbed die cutting, power knife system or similar means. Using any methods known in the art, perforations may also be added along the bottom edge 60, 66 of each of the back side 62 and the front side 68 to enable easier separation of the straps for use.

While particular embodiments of the present disclosure have been particularly shown and described with reference to specific embodiments, it should be apparent to those skilled in the art that the foregoing is illustrative only and not limiting, having been presented by way of example only. It is to be understood that the disclosed embodiments are merely examples of the disclosure, which may be embodied in various forms and detail without departing from the spirit and scope of the disclosure. Therefore, specific structural and functional details disclosed herein are not to be interpreted as limiting. Numerous other embodiments of a medical gown are contemplated as falling within the scope of the accompanying claims and equivalents thereto.

What is claimed is:

1. A medical gown comprising:
a torso portion comprising a front portion and a left and a right side portion connected on opposing sides thereto;
an upper portion extending upward from the torso portion, the upper portion comprising a left arm member and a right arm member configured to cover a left and right arm, respectively, of a wearer of the medical gown, the upper portion further comprising an opening configured to fit around a wearer's neck; and
a tie member having a first end integrally extending from one of the left and right side portions and a second end configured to be tied by a wearer, the tie member further including a first section that includes the second end, and a second section that includes the first end, and a folded edge connecting the first section to the second section, wherein the first section is disposed in a superposed folded position lengthwise on the second section, the first section being folded over lengthwise onto the second section at the folded edge, the second end being superposed onto the second section proximate the first end, each of the first section and the second section of the tie member further comprising detachably connected portions detachably connecting the tie member in the superposed folded position to the one of the left and right arm members that is proximate the one of the left and right side portions, the tie member being detachable via the detachably connected portions from the one of the left and right arm members in the superposed folded position for tying the folded edge around a waist of a wearer, and further configured to be unfolded along the folded edge and elongated by a wearer to form a larger closure for tying the second end around a waist of the wearer.

2. The medical gown of claim 1, wherein the first section and the second section are formed from separate strips of material, and the folded edge is formed from bonding edges of the first section and the second section together.

3. The medical gown of claim 1, the tie member being a left tie member having its first end integrally extending from the left side portion proximate the left arm member, the left tie member being detachably connected in the superposed folded position to the left arm member, the medical gown further comprising a right tie member having a first end integrally extending from the right side portion proximate the right arm member and a second end configured to be tied to the second end of the left tie member by a wearer, the right tie member further including a first section that includes the second end, and a second section that includes the first end, and a folded edge connecting the first section of the right tie member to the second section of the right tie member, wherein the first section of the right tie member is disposed in a superposed folded position lengthwise on the second section of the right tie member, the first section of the right tie member being folded over at the folded edge lengthwise onto the second section of the right tie member, the second end of the right tie member being superposed onto the second section of the right tie member proximate its first end, each of the first section and the second section of the right tie member further comprising detachably connected portions detachably connecting the right tie member in the superposed folded position to the right arm member, the right tie member being detachable via the detachably connected portions from the right arm member in the superposed folded position for tying the folded edge around a waist of a wearer, and further configured to be unfolded along the folded edge and elongated by a wearer to form a larger closure for tying the second end around a waist of the wearer.

4. The medical gown of claim 3, each of the left tie member and the right tie member operable to extend around the left and the right side portions and to tie together to form a closure around the wearer, a size of the closure being adjustable by unfolding one or both of the left tie member and the right tie member being tied together.

5. The medical gown of claim 1, wherein each of the detachably connected portions is formed from a perforated section of material detachably connecting the one of the left and the right arm members to each of the first section and the second section of the tie member.

6. The medical gown of claim 1, wherein each of the detachably connected portions is formed from one of a weak seam, an adhesive, and loose stitches detachably connecting the one of the left and the right arm members to the tie member.

7. The medical gown of claim 1, wherein the upper portion comprises a back side and a front side, wherein the right and the left arm members are formed by joining a portion of a bottom edge of each of the back side and the front side to form an enclosure configured to cover a wearer's arms.

8. The medical gown of claim 1, wherein the detachably connected portions of the tie member are adjacent the second end.

9. The medical gown of claim 7, wherein a top edge of the first section is detachably connected along the bottom edge of the front side and a top edge of the second section is detachably connected along the bottom edge of the back side.

10. The medical gown of claim 1, wherein no portion of the detachably connected tie member on the medical gown donned by a wearer, before being detached from the one of the left and right arm members, hangs below a bottom edge of the torso portion.

11. The medical gown of claim 1, wherein the medical gown is formed of a material and of a construction to provide fluid resistant protection to a wearer of the medical gown.

12. The medical gown of claim 11, the material further comprising an antimicrobial agent.

13. The medical gown of claim 1, each of the right and left arm members being a sleeve for fitting a wearer's arm therethrough and comprising a first opening for at least a portion of a wearer's hand, the gown further comprising a second opening for fitting a wearer's thumb therethrough.

14. The medical gown of claim 3, wherein each of the left and right tie members upon being detached and unfolded is sufficiently long to extend around the left and right sides, respectively, to the back of the medical gown, and further around the right and left sides, respectively, to tie together along the front side of the medical gown.

15. A medical gown comprising:
  a torso portion comprising a front portion and a left and a right side portion connected on opposing sides thereto;
  an upper portion extending upward from the torso portion, the upper portion comprising a left arm member and a right arm member configured to cover a left and right arm, respectively, of a wearer of the medical gown, the upper portion further comprising an opening configured to fit around a wearer's neck;
  a left tie member having a first end integrally extending from the left side portion proximate the left arm member and a second end configured to be tied by a wearer; and
  a right tie member having a first end integrally extending from the right side portion proximate the right arm member and a second end configured to be tied to the second end of the left tie member by a wearer;
  each of the left tie member and the right tie member further including a first section that includes the second end, and a second section that includes the first end, and a folded edge connecting the first section to the second section, wherein the first section is disposed in a superposed folded position lengthwise on the second section, the first section being folded over lengthwise onto the second section at the folded edge, the second end being superposed onto the second section proximate the first end, each of the first section and the second section of each of the left tie member and the right tie member further comprising detachably connected portions detachably connecting each of the left tie member and the right tie member in the superposed folded position to the left and the right arm member respectively, each of the left tie member and the right tie member being detachable via the detachably connected portions from the left and right arm member respectively in the superposed folded position for tying the folded edge of each of the left tie member and the right tie member around a waist of a wearer, each of the left tie member and the right tie member being further configured to be unfolded along the folded edge and elongated by a wearer to form a larger closure for tying the second end of each of the left tie member and the right tie member around a waist of the wearer.

16. The medical gown of claim 15, wherein the detachably connected portions of each of the left and the right tie member are proximate the second end of the left and right tie member, respectively.

17. The medical gown of claim 15, wherein the folded edge for each of the left and right tie members is a bonded edge formed from bonding edges of the first section and the second section together.

\* \* \* \* \*